United States Patent [19]
Platzek et al.

[11] Patent Number: 6,068,831
[45] Date of Patent: May 30, 2000

[54] PSEUDOPOLYROTAXANES

[75] Inventors: Johannes Platzek; Heribert Schmitt-Willich, both of Berlin, Germany

[73] Assignee: Schering Aktiengesellschaft, Germany

[21] Appl. No.: 09/214,498

[22] PCT Filed: Jun. 25, 1997

[86] PCT No.: PCT/EP97/03344

§ 371 Date: Dec. 30, 1998

§ 102(e) Date: Dec. 30, 1998

[87] PCT Pub. No.: WO98/01163

PCT Pub. Date: Jan. 15, 1998

[30] Foreign Application Priority Data

Jul. 9, 1996 [DE] Germany ............ 196 29 494

[51] Int. Cl.$^7$ ............ A61B 5/055; A61K 49/40
[52] U.S. Cl. ........... 424/9.36; 424/9.364; 424/9.363; 424/9.42; 424/9.35; 424/9.43; 514/58; 514/836; 536/46; 536/103; 536/121; 534/16
[58] Field of Search ............ 424/9.36, 9.363, 424/9.35, 9.364, 9.42, 9.43; 514/58, 836; 536/17.1, 46, 103, 121; 534/16; 436/173; 600/420

[56] References Cited

U.S. PATENT DOCUMENTS

| | | | |
|---|---|---|---|
| 4,986,980 | 1/1991 | Jacobsen | 424/9 |
| 5,336,762 | 8/1994 | Ranney | 534/16 |
| 5,855,900 | 1/1999 | Nobuhiko | 424/425 |

FOREIGN PATENT DOCUMENTS 0766968  4/1997  European Pat. Off. .

OTHER PUBLICATIONS

Harada, A. et al. Nature 364(6437):516–518, (Aug. 1993).
Raymo, F.M. et al. Trends in Polymer Science 4(7): 208–211, (Jul. 1996).
Cardenas, D.J. et al. J. American Chemical Society 119:2656–2664, (1997).

*Primary Examiner*—Gary E. Hollinden
*Attorney, Agent, or Firm*—Millen, White, Zelano & Branigan, P.C.

[57] ABSTRACT

The invention relates to new metal complex-containing or iodine-containing benzene derivatives that contain pseudopolyrotaxanes. They are valuable compounds for diagnosis. The pseudopolyrotaxane complexes have general formula (I), in which n represents the numbers 6, 7 or 8; m represents the numbers 2 to 50; X represents a direct bond or the radical —O—CO—CH(CH$_3$)—; R$_1$ and Y have the meaning that is indicated in the description and represent R$_3$—Y—R$_4$ polyalkylene glycols.

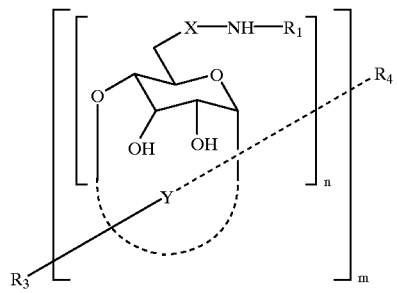

8 Claims, No Drawings

PSEUDOPOLYROTAXANES

This application is a 371 of PCT/EP97/03344 filed on Jun. 25, 1997.

The invention relates to the subject that is characterized in the claims, i.e., new pseudopolyrotaxanes, agents that contain these compounds, the use of these compounds in diagnosis, and a process for the production of these compounds and agents.

Pseudopolyrotaxanes are compounds in which several ring-shaped molecules are strung on a suitable polymer backbone. Such high-molecular molecule structures are described by, i.a., A. Harada et al., J. Am. Chem. Soc. 1994, 116, 3192–96 and G. Wenz et al., Angew. Chem. [Applied Chemistry] 104, 201–204 (1992).

The contrast media that are currently used in clinical practice for the modern imaging processes nuclear spin tomography (MRI) and computer tomography (CT) [Magnevist®, Pro Hance®, Ultravist® and Omniscan®] are dispersed throughout the entire extracellular space of the body (intravascular space and interstice). This dispersion space comprises about 20% of the body volume.

Clinically, extracellular MRI contrast media were first used successfully in the diagnosis of cerebral and spinal disease processes since here a quite special situation arises with respect to the regional dispersion space. In the brain and the spinal cord, extracellular contrast media in the healthy tissue cannot leave the intravascular space owing to the blood-brain barrier. In the case of pathological processes with disruption of the blood-brain barrier (e.g., malignant tumors, inflammations, demyelinating diseases, etc.), regions develop inside the brain with increased blood-vessel-permeability to these extracellular contrast media (Schmiedl et al., MRI of Blood-Brain Barrier Permeability in Astrocytic Gliomas: Application of Small and Large Molecular Weight Contrast Media, Magn. Reson. Med. 22: 288, 1991). By exploiting this disruption of vascular permeability, diseased tissue can be detected compared to healthy tissue with high contrast.

Outside of the brain and the spinal cord, however, there is no such permeability barrier to the above-mentioned contrast media (Canty et al., First-Pass Entry of Nonionic Contrast Agent into the Myocardial Extravascular Space. Effects on Radiographic Estimate of Transit Time and Blood Volume. Circulation 84: 2071, 1991). Thus, the concentration of the contrast medium no longer depends on vascular permeability, but rather only on the size of the extracellular space in the corresponding tissue. Delimitation of the vessels compared to the surrounding interstitial space using this contrast medium is not possible.

Especially for visualizing vessels, a contrast medium that disperses only into vascular space would be desirable. Such, a blood-pool agent should make it possible, with the aid of nuclear spin tomography, to delimit tissue that is well supplied with blood from tissue that is poorly supplied with blood and thus to diagnose an ischemia. It is also possible to delimit infarcted tissue, owing to its anemia, from surrounding healthy or ischemic tissue when a vascular contrast medium is used. This is of special importance if, e.g., the point is to distinguish a cardiac infarction from an ischemia.

To date, most patients in whom cardiovascular disease is suspected (this disease is the number-one cause of death in the Western industrialized countries) have to undergo invasive diagnostic studies.

There is therefore a need for NMR and x-ray contrast media that can label the vascular space (blood-pool-agent). These compounds are to be distinguished by good compatibility and high effectiveness (large increase in signal intensity in MRI).

To date, the attempt to solve at least a portion of this problem by using complexes that are bonded to macromolecules or biomolecules has been successful to an only very limited extent.

Thus, for example, the number of paramagnetic centers in the complexes, which are described in European Patent Applications No. 0 088 695 and No. 0 150 844, is not sufficient to ensure satisfactory imaging.

If the number of metal ions required is increased by repeatedly introducing complexing units into a macromolecular biomolecule, this is associated with an intolerable impairment of the affinity and/or specificity of this biomolecule [J. Nucl. Med. 24, 1158 (1983)].

Macromolecules can generally be suitable as contrast media for angiography. 24 hours after intravenous injection in rats, however, albumin-GdDTPA (Radiology 1987; 162: 205), e.g., shows a concentration in the liver tissue that amounts to almost 30% of the dose. In addition, only 20% of the dose is eliminated within 24 hours.

The macromolecule polylysine-GdDTPA (European Patent Application, Publication No. 0 233 619) also proved suitable as a blood-pool agent. For production-related reasons, however, this compound consists of a mixture of molecules of different sizes. During excretion tests in rats, it was shown that this macromolecule is excreted through the kidney unchanged by glomerular filtration. For synthesis-related reasons, however, polylysine-GdDTPA can also contain macromolecules that are so large that they cannot pass through the capillaries of the kidneys during glomerular filtration and thus remain in the body.

Macromolecular contrast media based on carbohydrates, e.g., dextran, have also been described (European Patent Application, Publication No. 0 326 226). The drawback of these compounds lies in the fact that the latter generally carry only about 5% of the signal-enhancing paramagnetic cations.

The object was therefore to make available new diagnostic agents mainly for detecting and locating vascular diseases, which do not have the above-mentioned drawbacks. This object is achieved by this invention.

The pseudopolyrotaxanes according to the invention can be described by general formula I

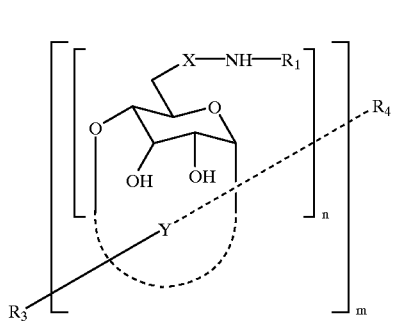

in which n means the numbers 6, 7 or 8, m means the numbers 2 to 50,

X means a direct bond or the radical —O—CO—CH(CH$_3$)—,

R$_1$ means the opacifying radicals

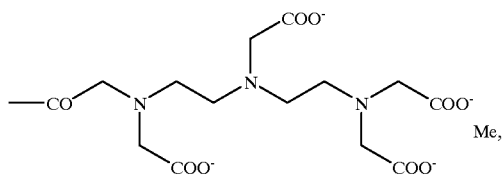
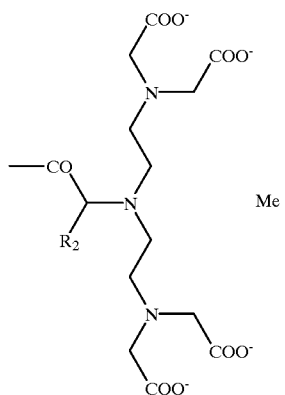
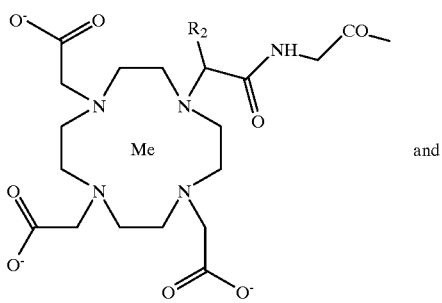
and
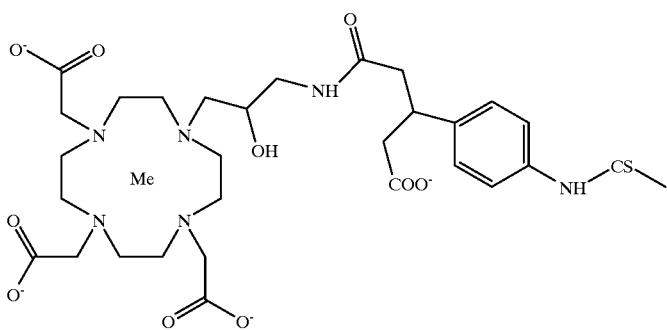
with $R_2$ meaning hydrogen, $-(CH_2)_{1-3}-COOH$, straight-chain or branched ($C_1$–$C_4$)-alkyl, straight-chain or branched ($C_1$–$C_4$)-hydroxyalkyl, phenyl or benzyl, Me as a metal cation of an element of atomic numbers 21 to 29, 39, 42, 44 or 57–83 as well as optionally cations of inorganic and/or organic bases, amino acids or amino acid amides or $R_1$ meaning

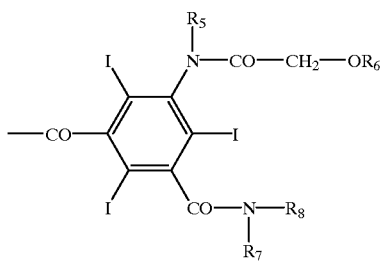

with
R$_5$ meaning hydrogen or C$_1$–C$_2$ alkyl or a —(CH$_2$)$_{1-3}$—COOH group,
R$_6$ meaning hydrogen or methyl, and
R$_7$, R$_8$, the same or different, meaning hydrogen or straight-chain alkyl with 2–6 C atoms or branched-chain alkyl with 3–6 C atoms, whereby both alkyl radicals can be substituted with 1–5 OH groups,
R$_3$ stands for the hydroxy or C$_1$–C$_2$ alkoxy group,
R$_4$ stands for the hydroxy, methyl or methoxy group,
Y means radicals —(CH$_2$)$_p$[O—CH$_2$—CH$_2$]$_o$,

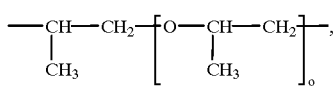

in which
o means the numbers 10–200, and
p means the numbers 2–20
or
Y means the radical —[CH$_2$]$_{10}$—CO—NH—[CH$_2$]$_2$—, whereby in the latter case, R$_4$ stands for —N(R$_{10}$)—Z[N(R$_{10}$)$_2$]$_2$ and R$_3$ stands for the radical —NH R$_9$, in which R$_9$ represents hydrogen and benzyloxycarbonyl,

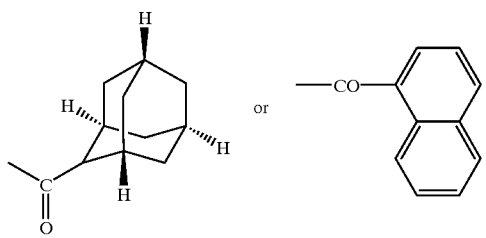

R$_{10}$ represents the radical

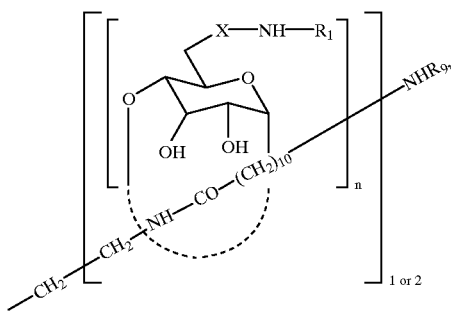

with the above-indicated meanings for n, R$_1$ and R$_9$, and z represents the radical

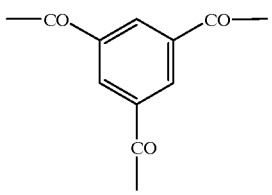

The preferred range for m is 5–30.

As a straight-chain (C$_1$–C$_4$)-hydroxyalkyl, R$_2$ means hydroxymethyl, 2-hydroxyethyl, 2-hydroxy-propyl, 3-hydroxypropyl, 2-, 3- or 4-hydroxy-n-butyl.

As a branched-chain (C$_3$–C$_4$)-alkyl, R$_2$ means isopropyl, sec-butyl, tert-butyl, isobutyl.

As a branched-chain (C$_3$–C$_4$)-hydroxyalkyl, R$_2$ is defined as the following radicals:
1-Hydroxy-1-methylethyl, 2-hydroxy-1-methylethyl, 1-hydroxy-sec-butyl, 1-hydroxymethyl-n-propyl, 1-hydroxy-isobutyl, 2-hydroxyisobutyl, 3-hydroxy-2-methyl-n-propyl and 2-hydroxy-1,1-dimethyl-ethyl.

As straight-chain or branched alkyl groups with up to 6 C atoms, which can be substituted by 1–5 hydroxy groups, R$_7$ and R$_8$ preferably mean the groups already mentioned for R$_2$ as well as n-pentyl, isopentyl, neopentyl, n-hexyl, sec-hexyl, isohexyl, 2-ethyl-n-butyl.

As hydroxylated groups, mainly the following are suitable:

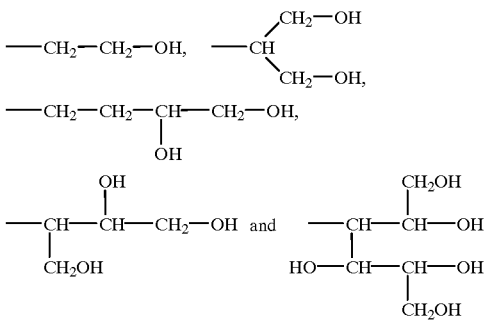

For o, in addition to the above-mentioned number range of 10–200, preferably the number range of 25–100 is suitable.

If the agent according to the invention is intended for use in NMR diagnosis, the central ion of the complex salt has to be paramagnetic. These are especially the divalent and trivalent ions of the elements of atomic numbers 21–29, 42, 44 and 58–70. Suitable ions are, for example, the chromium (III), iron(II), cobalt(II), nickel(II), copper(II), praseodymium(III), neodymium(III), samarium(III) and ytterbium(III) ions. Because of their very strong magnetic moment, the gadolinium(III), terbium(III), dysprosium(III), holmium(III), erbium(III), manganese(II) and iron(III) ions are especially preferred.

If the agent according to the invention is intended for use in diagnostic radiology, the central ion has to be derived from an element of a higher atomic number to achieve sufficient absorption of x rays. It has been found that diagnostic agents that contain a physiologically compatible complex salt with central ions of elements of atomic numbers between 21–29, 39, 42, 44, 57–83 are suitable for this purpose; these are, for example, the lanthanum(III) ion and the above-mentioned ions of the lanthanide series.

The pseudopolyrotaxane complexes according to the invention contain at least 12 ions of an element of the above-mentioned atomic number.

The residual acid hydrogen atoms, i.e., those that have not been substituted by the central ion, can optionally be replaced completely or partially by cations of inorganic and/or organic bases, amino acids or amino acid amides.

Suitable inorganic cations are, for example, the lithium ion, the potassium ion, the calcium ion, the magnesium ion and especially the sodium ion. Suitable cations of organic bases are, i.a., those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine and ornithine as well as the amides of otherwise acid or neutral amino acids.

The compounds according to the invention, which have a molecular weight of 10,000–100,000, preferably 20,000–60,000 Da, exhibit the above-mentioned desired properties. They contain the large number of metal ions, that are required for their use, bound in a stable manner in the complex.

The new pseudopolyrotaxanes build up in regions with elevated vascular permeability, such as, e.g., in tumors, make it possible to make statements on the perfusion of tissues, provide the opportunity to determine the blood volume in tissues, to shorten the relaxation times or densities of the blood in a selective manner, and to display graphically the permeability of the blood vessels. Such physiological information cannot be obtained by using extracellular contrast media, such as, e.g., Gd-DTPA [Magnevist®]. From these standpoints also emerge the uses in the modern imaging processes of nuclear spin tomography and computer tomography: more specific diagnoses of malignant tumors, early therapy monitoring in the case of cytostatic, antiphlogistic or vasodilatative therapy, early detection of underperfused regions (e.g., in the myocardium), angiography in vascular diseases, and detection and diagnosis of (sterile or infectious) diseases. In addition, the pseudopolyrotaxane complexes according to the invention are extremely well suited for displaying the lymphatic vessels (interstitial and intravenous lymphography).

As further advantages over extracellular contrast media, such as, e.g., Gd-DTPA [Magnevist®], the elevated effectiveness as contrast media for nuclear spin tomography (elevated relaxivity) has to be emphasized, which leads to a significant reduction of the diagnostically necessary dose. At the same time, the contrast media according to the invention can be formulated as solutions in an isoosmolar manner with regard to the blood, and thus reduce the osmotic burdening of the body, which is reflected in a reduced toxicity of the substance (higher toxic threshold). Lower doses, and higher toxic thresholds result in a significant increase of the reliability of contrast medium uses in modern imaging processes.

Compared to other macromolecular contrast media based on carbohydrates, e.g., dextran (European Patent Application, Publication No. 0 326 226), which—as mentioned—generally carry only about 5% of the signal-enhancing paramagnetic cation, the pseudopolyrotaxane complexes according to the invention have a content of generally about 10–20% of the paramagnetic cation. Thus, the macromolecules according to the invention produce per molecule a very much higher signal enhancement, which at the same time leads to the fact that the dose that is necessary for nuclear spin tomography is considerably smaller.

It has been possible with the pseudopolyrotaxane complexes according to the invention to make available high-molecular contrast media, which, surprisingly enough, are completely eliminated, although the average molecular weight, in some cases, is considerably above the kidney filtration threshold.

Compared to the other mentioned polymer compounds of the prior art, the complexes according to the invention are distinguished by improved excretion behavior, greater effectiveness, greater stability and/or better compatibility.

Another advantage of this invention lies in the fact that now complexes with hydrophilic or lipophilic, macrocyclic or open-chain, low-molecular or high-molecular ligands have become accessible. In addition, the opportunity is provided to control compatibility and pharmacokinetics of these polymer complexes by chemical substitution.

The production of the pseudopolyrotaxane complexes according to the invention is carried out in that compounds of general formula II,

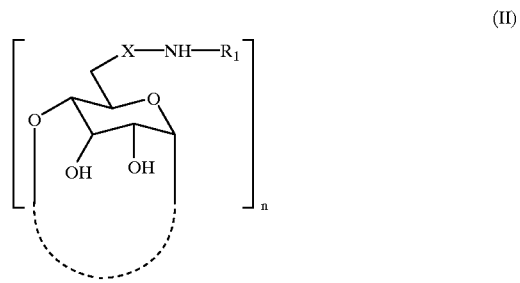

(II)

in which X, $R_1$ and n have the above-indicated meanings, are reacted with compounds of Formula III

(III), in which Y and $R_3$ have the above-indicated meanings, and $R_{11}$ means hydroxy, methyl, methoxy or, if Y stands for —$(CH_2)_{10}$—CO—NH$(CH_2)_2$, the radical —N$(R_{12})$Z[N$(R_{12})_2]_2$, $R_{12}$ represents the radical —$(CH_2)_2$—NH—CO—$(CH_2)_{10}$—NHR$_9$ with $R_9$ in the above-indicated meaning, as described in, e.g., J. Am. Chem. Soc. 116, 3192 (1994).

The starting substances of general formula III can either be obtained commercially (e.g., Aldrich) or produced analogously to the process that is disclosed in Example 3. The educts of general formula II are obtained analogously to the processes that are disclosed in the examples by using cyclodextrin-oligo-amines that are known in the literature or by using amino acid esters of cyclodextrins, which are reacted in an amidic manner with carboxylic acid-activated complexes or complex ligands or triiodinated benzene derivatives, as indicated for $R_1$ (see, e.g., DE 39 38992, WO 93/10824, DE 4 4258 57).

The purification of the pseudopolyrotaxane complexes that are obtained is carried out optionally after the pH is set at 6 to 8, preferably about 7, by adding an acid or a base, preferably by ultrafiltration with membranes of suitable pore size (e.g., Amicon® XM30, Amicon® YM10, Amicon® YM3) or gel filtration on, e.g., suitable Sephadex® gels.

The production of the pharmaceutical agents according to the invention is also carried out in a way known in the art by the complex compounds according to the invention—optionally with the addition of additives that are commonly used in galenicals—being suspended or dissolved in aqueous medium, and then the suspension or solution optionally being sterilized. Suitable additives are, for example, physiologically harmless buffers (such as, for example, tromethamine), additions of complexing agents or weak complexes (such as, for example, diethylenetriaminepentaacetic acid or the corresponding calcium-pseudorotaxane complexes) or—if necessary—electrolytes such as, for example, sodium chloride or—if necessary, antioxidants such as, for example, ascorbic acid.

If suspensions or solutions of the agents according to the invention in water or physiological salt solution are desired for enteral administration or other purposes, they are mixed with one or more adjuvant(s) that are commonly used in galenicals [for example, methyl cellulose, lactose, mannitol] and/or surfactant(s) [for example, lecithins, Tween®, Myrj®] and/or flavoring substance(s) for taste correction [for example, ethereal oils].

The pharmaceutical agents according to the invention preferably contain 1 μmol–1 mol/l of complex salt and are generally dosed in amounts of 0.0001–5 mmol/kg. They are intended for enteral and parenteral administration. The complex compounds according to the invention are used for NMR diagnosis and diagnostic radiology in the form of their complexes with the ions of the elements with atomic numbers 21–29, 39, 42, 44 and 57–83.

The agents according to the invention meet the varied requirements for suitability as contrast media for nuclear spin tomography. They are thus extremely well suited in this regard to improve in its informational value the image that is obtained with the aid of nuclear spin tomographs after enteral or parenteral administration by increasing signal intensity. They also show the high effectiveness that is necessary to load the body with the lowest possible amounts of foreign substances and the good compatibility that is necessary to maintain the noninvasive character of the studies.

The good water-solubility and low osmolality of the agents according to the invention make it possible to produce highly-concentrated solutions so that the volume burden of the circulatory system is kept within reasonable limits and the dilution by bodily fluid is compensated for, i.e., NMR diagnostic agents have to be 100- to 1000-fold more water-soluble than those for NMR spectroscopy. In addition, the agents according to the invention have not only high in-vitro stability, but also surprisingly high in-vivo stability, so that a release or an exchange of the ions—toxic in themselves—that are not covalently bonded to the complexes is carried out only extremely slowly within the time in which the new contrast media are completely excreted again.

In general, the agents according to the invention are dosed for use as NMR diagnostic agents in amounts of 0.001–5 mmol/kg, preferably 0.005–0.5 mmol/kg. Details of use are discussed in, for example, H.-J. Weinmann et al., Am. J. of Roentgenology 142, 619 (1984).

Especially low dosages (below 1 mg/kg of body weight) of organ-specific NMR diagnostic agents can be used, for example, for detecting tumors and myocardial infarctions.

The complex compounds according to the invention can also be used advantageously as susceptibility reagents and as shift reagents for in-vivo NMR spectroscopy.

In the in-vivo administration of the therapeutic agents according to the invention, the latter can be administered together with a suitable vehicle, such as, for example, serum or physiological common salt solution, and together with another protein, such as, for example, human serum albumin. In this case, the dosage depends on the type of cellular disorder, the metal ion used and the type of imaging method.

The therapeutic agents according to the invention are administered parenterally, preferably i.v.

In general, the agents according to the invention are dosed for use as x-ray contrast media analogously to, e.g., meglumine-diatrizoate in amounts of 0.1–5 mmol/kg, preferably 0.25–1 mmol/kg.

Details of use of x-ray contrast media are discussed in, for example, Barke, Röntgenkontrastmittel [X-Ray Contrast Media], G. Thieme, Leipzig (1970) and P. Thurn, E. B ücheler "Einführung in die Röntgendiagnostik [Introduction in Diagnostic Radiology],"G. Thieme, Stuttgart, New York (1977).

In general, it has been possible to synthesize new metal complex-containing and iodine-containing pseudopolyrotaxanes, which open up new possibilities in diagnosis.

The following examples are used for a more detailed explanation of the subject of the invention:

EXAMPLE 1 a) Hexa-(Gd-DTPA-monoamide) Derivative of 6,6',6'',6''',6'''',6'''''-hexaamino-6,6',6'',6''',6'''',6'''''-hexadeoxy-α-cyclodextrin 1.26 g (1 mmol) of 6,6',6'',6''',6'''',6'''''-hexaamino-6,6',6'',6''',6'''',6'''''-hexadeoxy-α-cyclodextrin-hexahydrochloride [J. Boger, R. J. Corcoran and J.-M. Lehn, Helv. Chim. Acta 61, 2190–2218 (1978)] is dissolved in 80 ml of water. Within a half hour, 7.26 g (18 mmol) of $N^3$-(2,6-dioxomorpholinoethyl)-$N^6$-(ethoxycarbonylmethyl)-3,6-diazaoctanedioic acid (Example 13a of EP 0331 616) is then added in portions in solid form, whereby the pH is kept at 7.5–8 by adding 1N sodium hydroxide solution. Then, for saponification of ethyl esters, additional 1N sodium hydroxide solution up to a pH>13 is added and allowed to stir for 3 hours at this pH. Then, the alkaline solution is set at pH 5 with Amberlite IR 120 ($H^+$ form), ion exchanger is suctioned off, and it is mixed with 4.75 g of $GdCl_3$ (18 mmol), stirred for 30 minutes at 80° C., set at pH 7.2 with 1N sodium hydroxide solution, and the solution that is produced is ultrafiltered (AMICON® YM 1 membrane). The solution from which low-molecular components are removed is ultimately freeze-dried. 4.38 g (94.4% of theory) of a colorless, flocculent powder is obtained.

$H_2O$ content (Karl Fischer): 7.8%

Gd determination (AAS): 20.1%

Elementary analysis (relative to anhydrous substance):

| Cld: | C 33.71 | H 3.96 | N 7.86 | Gd 22.06 | Na 3.23 |
|---|---|---|---|---|---|
| Fnd: | C 33.97 | H 4.22 | N 7.69 | Gd 21.48 | Na 2.80 | b) Polyrotaxane that Consists of Methoxypolyethylene Glycol and the α-cyclodextrin-hexa-Gd Complex that is Described in Example 1a 928 mg (0.2 mmol) of the hexa-(GdDTPA-monoamide) derivative of 6,6',6'',6''',6'''',6'''''-hexaamino-6,6',6'',6''',6'''',6'''''-hexadeoxy-α-cyclodextrin that is described in Example 1a is dissolved in 5 ml of water and mixed with 10 mg (5 μmol) of methoxypolyethylene glycol (Sigma, M=2000) while being stirred. The solution is irradiated for 10 minutes in an ultrasonic bath and then stirred overnight at room temperature. For separation of low-molecular components, filtering is done using a 15 ml AMICON® centrifuging unit centriplus-3® (cut off 3,000 Dalton) and then freeze-dried. 430 mg of colorless, flocculent lyophilizate is obtained.

H₂O content (Karl Fischer): 4.7%

Gd determination (AAS): 20.3%

Elementary analysis (relative to anhydrous substance):

| Cld: | C 34.13 | H 4.06 | N 7.70 | Gd 21.62 | Na 3.16 |
|---|---|---|---|---|---|
| Fnd: | C 34.07 | H 4.34 | N 7.46 | Gd 21.33 | Na 2.87 |

Photon correlation spectroscopy shows numerical mean values of >30 nm for the hydrodynamic particle size.

EXAMPLE 2 a) 6,6',6'',6''',6'''',6''''',6''''''-Heptaamino-6,6',6'',6''',6'''',6''''', 6''''''-heptadeoxy-β-cyclodextrinheptahydrochloride 1.90 g (1 mmol) of 6,6',6'',6''',6'''',6''''',6''''''-heptaamino-6,6',6'',6''',6'''',6''''',6''''''-heptadeoxy-β-cyclodextrin-2,2',2'', 2''',2'''',2''''',2'''''', 3,3',3'',3''',3'''',3''''',3''''''-tetradecaacetate [J. Boger et al., Helv. Chim. Acta 61, 2190–2218 (1978) is dissolved in dioxane/methanol (10:1), and after 14 ml (28 mmol) of 2N sodium hydroxide solution is added, it is stirred for 2 hours at room temperature and then set at pH 7 with dilute hydrochloric acid. The neutralized solution is evaporated to the dry state in a vacuum, the residue is washed in succession with chloroform and water and again evaporated to the dry state. The heptakis(6-azido-6-deoxy)-β-CD that is obtained is suspended under nitrogen in dioxane/methanol (5:1), mixed with 5.25 g (20 mmol) of triphenylphosphine, the solution that is produced is stirred for one hour at room temperature and then mixed with concentrated ammonia. After stirring overnight, it is evaporated to the dry state in a vacuum, taken up with water and set at pH 6 with 1N hydrochloric acid, and the solution is freeze-dried. 1.33 g of colorless, flocculent powder (85% of theory) is obtained.

H₂O content (Karl Fischer): 11.5%

Elementary analysis (relative to anhydrous substance):

| Cld: | C 36.47 | H 6.12 | N 7.09 | Cl 17.94 |
|---|---|---|---|---|
| Fnd: | C 36.77 | H 6.21 | N 6.86 | Cl 17.71 | b) Hepta-(Gd-DTPA-monoamide) Derivative of 6,6',6'',6''', 6'''',6''''',6''''''-heptaamino-6,6',6'',6''',6'''',6''''',6''''''-heptadeoxy-β-cyclodextrin 782 mg (0.5 mmol) of the heptakis (6-amino-6-deoxy)-β-CD-heptahydrochloride that is described in Example 2a above is dissolved in 80 ml of water. Within a half hour, 4.24 g (10.5 mmol) of $N^3$-(2,6-dioxomorpholinoethyl)-$N^6$-(ethoxycarbonylmethyl)-3,6-diazaoctanedioic acid (Example 13a of EP 0331 616) is then added in portions in solid form, whereby the pH is kept at 7.5–8 by adding 1N sodium hydroxide solution. Then, another 1N sodium hydroxide solution up to a pH>13 is added for saponification of the ethyl esters, and it is allowed to stir for 3 hours at this pH. Then, the alkaline solution is set at pH 5 with Amberlite IR 120 (H⁺ form), ion exchanger is suctioned off, and it is mixed with 2.77 g of GdCl₃ (10.5 mmol), stirred for 30 minutes at 80° C., set at pH 7.2 with 1N sodium hydroxide solution, and the solution that is produced is ultrafiltered (AMICON® YM-1 membrane). The solution from which low-molecular components are removed is ultimately freeze-dried. 2.49 g (91.1% of theory) of colorless, flocculent powder is obtained.

H₂O content (Karl Fischer): 8.6%

Gd determination (AAS): 19.9%

Elementary analysis (relative to anhydrous substance):

| Cld: | C 33.71 | H 3.96 | N 7.86 | Gd 22.06 | Na 3.23 |
|---|---|---|---|---|---|
| Fnd: | C 33.85 | H 4.11 | N 7.70 | Gd 21.83 | Na 3.06 | c) Polyrotaxane that Consists of Poly-(1,2-propanediol) and the β-cyclodextrin-hepta-Gd Complex that is Described in Example 2b 1.09 g (0.2 mmol) of the hepta-(GdDTPA-monoamide) derivative of 6,6',6'',6''',6'''',6''''',6''''''-heptaamino-6,6',6'',6''', 6'''',6''''',6''''''-heptadeoxy-β-cyclodextrin that is described in Example 2b is dissolved in 10 ml of water and mixed with 20 μl (0.02 mmol) of poly-(1,2-propanediol) while being stirred (Aldrich, $M_W$=1000), whereby the polymer droplets dissolve gradually. The solution is irradiated for 10 minutes in an ultrasonic bath and then stirred overnight at room temperature. For separation of low-molecular components, filtering is done using a 15 ml AMICON® centrifuging unit centriplus-3® (cut off 3,000 Dalton) and then freeze-dried. 620 mg of colorless, flocculent lyophilizate is obtained.

H₂O content (Karl Fischer): 7.9%

Gd determination (AAS): 19.7%

Elementary analysis (relative to anhydrous substance):

| Cld: | C 34.35 | H 4.11 | N 7.68 | Gd 21.56 | Na 3.15 |
|---|---|---|---|---|---|
| Fnd: | C 34.09 | H 3.86 | N 7.73 | Gd 21.70 | Na 2.94 |

Photon correlation spectroscopy shows numerical mean values of >30 nm for the hydrodynamic particle size.

EXAMPLE 3 a) Bis[2-(benzyloxycarbonylamino)-ethyl]-amine 5.15 g (50 mmol) of diethylenetriamine and 13.9 ml (100 mmol) of triethylamine are dissolved in dichloromethane and mixed at −20° C. with 16.1 g of benzyl cyanoformate (Fluka) in dichloromethane, and then it is stirred overnight at room temperature. After the reaction has been completed, it is evaporated during draw-off, the residue is taken up in diethyl ether, the organic phase is washed with sodium carbonate solution and dried with sodium sulfate. The filtrate is mixed with hexane, the precipitate is filtered off and dried.

Yield: 16.34 g (88% of theory)

Elementary analysis:

| Cld: | C 64.67 | H 6.78 | N 11.31 |
|---|---|---|---|
| Fnd: | C 64.48 | H 6.85 | N 11.19 | b) N,N,N',N',N'',N''-Hexakis[2-(benzyloxycarbonylamino)-ethyl]-Trimesic Acid Triamide 1.33 g (5 mmol) of trimesic acid-trichloride (Aldrich) and 3.47 ml (25 mmol) of triethylamine are dissolved in dimethylformamide (DMF) and mixed at 0° C. with 6.5 g (17.5 mmol) of the amine that is described in Example 3a and then stirred overnight at room temperature. The solution is concentrated by evaporation in a vacuum, and the residue is chromatographed with ethyl acetate on silica gel.

Yield: 3.94 g (62% of theory)

Elementary analysis:

| Cld: | C 65.24 | H 5.95 | N 9.92 |
|---|---|---|---|
| Fnd: | C 65.47 | H 6.03 | N 9.82 | c) N,N,N',N',N",N"-Hexakis[14-(benzyloxycarbonylamino)-4-oxo-3-aza-tetradecyl]trimesic Acid Triamide 1.27 g (1 mmol) of the hexa-benzyloxycarbonylamine that is described in Example 3b is dissolved in glacial acetic acid and mixed with 33% hydrogen bromide in glacial acetic acid while being stirred. After 60 minutes, the incipient precipitation is completed with diethyl ether, the hexaamine-hydrobromide that is produced is washed with ether, dried in a vacuum and used in the reaction described below without additional purification.

Yield: 0.95 g (quantitative)

2.52 g (7.5 mmol) of N-benzyloxycarbonylamino-undecanoic acid (H. N. Rydon et al., J. Chem. Soc. 1965, 4246–53), 1.2 g (7.5 mmol) of 1-hydroxybenzotriazole and 2.4 g (7.5 mmol) of 2-(1H-benzotriazol-1-yl)-1,1,3,3-tetramethyluronium tetrafluoroborate (TBTU; Peboc Limited, UK) are dissolved in DMF and stirred for 15 minutes. This solution is then mixed with 5.16 ml (30 mmol) of N-ethyldiisopropylamine and with 0.95 g (1 mmol) of the above-described hexa-amine-hydrobromide, and it is stirred overnight at room temperature. After the reaction has been completed, it is concentrated by evaporation in a vacuum, and the residue is chromatographed on silica gel with ethyl acetate/ethanol (2:1).

Yield: 1.92 g (81% of theory)

Elementary analysis:

| Cld: | C 68.41 | H 8.55 | N 8.86 |
|---|---|---|---|
| Fnd: | C 68.20 | H 8.72 | N 8.74 | d) Polyrotaxane that Consists of N,N,N',N',N",N"-hexakis[14-(benzyloxycarbonylamino)-4-oxo-3-aza-tetradecyl] trimesic Acid Triamide and the β-cyclodextrin-hepta-Gd Complex that is Described in Example 2b 1.09 g (0.2 mmol) of the hepta-(GdDTPA-monoamide) derivative of 6,6',6",6"',6"",6""',6""""-heptaamino-6,6',6",6"', 6"",6""',6""""-heptadeoxy-β-cyclodextrin that is described in Example 2b is dissolved in 10 ml of water and mixed with 47 mg (0.02 mmol) of the hexamers that are described in Example 3c above while being stirred. The suspension is irradiated for 10 minutes in an ultrasonic bath and then stirred overnight at room temperature. For separation of low-molecular components, filtering is done using a 15 ml AMICON® centrifuging unit centriplus-10® (cut off 10,000 Dalton), and then it is freeze-dried. 1.13 g of colorless, flocculent lyophilizate is obtained.

H$_2$O content (Karl Fischer): 8.6%

Gd determination (AAS): 19.7%

Elementary analysis (relative to anhydrous substance, calculated as 14-rotaxane, i.e., on average consists of 2.33 β-CD's per arm):

| Cld: | C 34.84 | H 4.11 | N 7.89 | Gd 21.34 | Na 3.12 |
|---|---|---|---|---|---|
| Fnd: | C 34.76 | H 3.89 | N 7.62 | Gd 21.05 | Na 2.90 |

EXAMPLE 4 a) 10-[5-(2-Carboxyphenyl)-2-hydroxy-5-oxo-4-azapentyl]-1,4,7-tris(carboxymethyl)-1,4,7,10-tetraazacyclododecane 50 g (144.3 mmol) of 1,4,7-tris(carboxymethyl)-1,4,7,10-tetraazacyclododecane (DO3A) is dissolved in 250 ml of water, and the pH is set at 13 with 5N sodium hydroxide solution. Then, a solution of 38.12 g (187.6 mmol) of N(2,3-epoxypropyl)phthalimide (Aldrich) in 100 ml of dioxane is added in drops within one hour, stirred for 24 hours at 50° C., and the pH is kept at 13 by adding 5N sodium hydroxide solution. The solution is set at pH 2 with 10% hydrochloric acid and evaporated to the dry state in a vacuum. The residue is dissolved in some water and purified on an ion-exchange column (Reillex®=poly-(4-vinyl) pyridine (it is eluted with water). The main fractions are concentrated by evaporation in a vacuum, and final purification of the residue is achieved by chromatography on RP-18 (LiChroPrep®/mobile solvent: gradient that consists of tetrahydrofuran/methanol/water). After the main fractions are concentrated by evaporation, 63.57 g (71% of theory) of an amorphous solid is obtained.

Water content: 8.5%

Elementary analysis (relative to anhydrous substance):

| Cld: | C 52.90 | H 6.57 | N 12.34 |
|---|---|---|---|
| Fnd: | C 52.65 | H 6.68 | N 12.15 | b) 10-(3-Amino-2-hydroxy-propyl)-1,4,7-tris (carboxymethyl)-1,4,7,10-tetraazacyclododecane 50 g (88.1 mmol) of the title compound from Example 4a is refluxed in 300 ml of concentrated hydrochloric acid for 24 hours. It is evaporated to the dry state, the residue is dissolved in some water and purified on an ion-exchange column (Reillex®=poly-(4-vinyl)pyridine (it is eluted with water). The main fractions are evaporated to the dry state.

Yield: 39.0 g (95% of theory) of a vitreous solid

Water content: 10.3%

Elementary analysis (relative to anhydrous substance):

| Cld: | C 48.68 | H 7.93 | N 16.70 |
|---|---|---|---|
| Fnd: | C 48.47 | H 8.09 | N 16.55 | c) Gadolinium Complex of 10-(3-amino-2-hydroxy-propyl)-1,4,7-tris(carboxymethyl)-1,4,7,10-tetraazacyclododecane 38 g (90.6 mmol) of the title compound from Example 4b is dissolved in 300 ml of water, and 16.42 g (45.3 mmol) of gadolinium oxide is added. It is heated for 3 hours to 90° C. The cooled solution is stirred with 5 ml each of acidic ion exchanger (IR-120/H$^+$ form) and 5 ml of basic exchanger (IRA-410/OH$^-$ form) for one hour at room temperature. Exchanger is filtered out. Freeze-drying of the filtrate yields 57.23 g (98% of theory) of an amorphous solid.

Water content: 11.3%

Elementary analysis (relative to anhydrous substance):

| Cld: | C 35.59 | H 5.27 | Gd 27.41 | N 12.21 |
|---|---|---|---|---|
| Fnd: | C 35.32 | H 5.38 | Gd 27.20 | N 12.31 | d) Gadolinium Complex of 10-[7-(4-nitrophenyl)-2-hydroxy-5-oxo-7-(carboxymethyl)-4-aza-heptyl]-1,4,7-tris(carboxymethyl)-1,4,7,10-tetraazacyclododecane 9.84 g (41.8 mmol) of 3-(4-nitrophenyl)-glutaric acid anhydride is added to 20 g (34.86 mmol) of the title compound from Example 4c in 200 ml of dimethylformamide/20 ml of triethylamine (Journal of Org. Chem., Vol. 26, 3856 (1961)), and it is stirred overnight at room temperature. It is evaporated to the dry state in a vacuum. The residue is recrystallized from isopropanol/acetic acid 95:5.

Yield: 27.46 g (94% of theory) of a yellowish solid
Water content: 3.4%
Elementary analysis (relative to anhydrous substance):

| Cld: | C 41.58 | H 4.86 | Gd 19.44 | N 10.39 |
|---|---|---|---|---|
| Fnd: | C 41.38 | H 4.97 | Gd 19.28 | N 10.17 | e) Gadolinium Complex of 10-[7-(4-aminophenyl)-2-hydroxy-5-oxo-7-(carboxymethyl)-4-aza-heptyl]-1,4,7-tris(carboxymethyl)-1,4,7,10-tetraazacyclododecane 25 g (30.9 mmol) of the title compound from Example 4d is dissolved in 250 ml of methanol, and 5 g of palladium catalyst (10% Pd on C) is added. It is hydrogenated overnight at room temperature. The catalyst is filtered off, and the filtrate is evaporated to the dry state in a vacuum.

Yield: 24.07 g (97% of theory) of a cream-colored solid
Water content: 3.0%
Elementary analysis (relative to anhydrous substance):

| Cld: | C 43.18 | H 5.31 | Gd 20.19 | N 10.79 |
|---|---|---|---|---|
| Fnd: | C 43.27 | H 5.48 | Gd 20.02 | N 10.61 | f) Gadolinium Complex of 10-[7-(4-isothiocyanatophenyl)-2-hydroxy-5-oxo-7-(carboxy-methyl)-4-aza-heptyl]-1,4,7-tris(carboxymethyl)-1,4,7,10-tetraazacyclododecane 15 g (19.26 mmol) of the title compound from Example 4e is dissolved in 100 ml of water, and 6.64 g (57.8 mmol) of thiophosgene in 50 ml of chloroform is added. It is stirred for 1 hour at 50° C. It is cooled to room temperature, the organic phase is separated, and the aqueous phase is shaken out twice with 100 ml of chloroform. The aqueous phase is evaporated to the dry state, and the residue is absorptively precipitated in 100 ml of isopropanol at room temperature. The solid is filtered off and washed with ether. After drying overnight in a vacuum (40° C.), 15.9 g (98% of theory) of a cream-colored solid is obtained.

Water content: 3.5%
Elementary analysis (relative to anhydrous substance):

| Cld: | C 42.43 | H 4.79 | Gd 19.15 | N 10.24 | S 3.91 |
|---|---|---|---|---|---|
| Fnd: | C 42.23 | H 4.90 | Gd 19.01 | N 10.05 | S 3.96 | g) 6,6',6",6"',6"",6""'-Hexakis(N-fluorenylmethoxycarbonylalanyl)-α-cyclodextrin 2.08 g (2 mmol; water content 7%) of α-cyclodextrin is dissolved in dimethylformamide, mixed with benzene and dehydrated azeotropically. It is then cooled to 0° C., 1.32 ml (12 mmol) of N-methylmorpholine is added, and after 4.05 g (12 mmol) of N-fluorenylmethoxycarbonyl-alanine-N-carboxylic acid anhydride, Fmoc-Ala-NCA (propeptides, SNPE GmbH, Frankfurt/M) is added, it is stirred overnight at room temperature. The solution is then concentrated by evaporation in a vacuum, the residue is washed with water and ultimately recrystallized from ethyl acetate.

Yield: 5.08 g (93% of theory)
Elementary analysis (relative to anhydrous substance):

| Cld: | C 63.29 | H 5.53 | N 3.08 |
|---|---|---|---|
| Fnd: | C 63.14 | H 5.70 | N 2.98 | h) Hexa-thiourea Conjugate that Consists of Hexakis-(O-alanyl)-α-CD with the gadolinium Complex of 10-[7-(4-isothiocyanatophenyl)-2-hydroxy-5-oxo-7-(carboxymethyl)-4-azaheptyl]-1,4,7-tris(carboxymethyl)-1,4,7,10-tetraazacyclododecane 2.78 g (1 mmol) of the hexakis-[O-(Fmoc-alanyl)]-α-CD's described in Example 4g above is dissolved in dimethylformamide and mixed with 4 g of 4-dimethylaminopyridine. After 15 minutes, of stirring at room temperature, 5.31 g (6.3 mmol) of the isothiocyanate that is described in Example 4f is added, and it is stirred overnight. The solution is then concentrated by evaporation in a vacuum, taken up with water, set at pH 7, and low-molecular portions are removed via an AMICON® ultrafiltration membrane YM 1. After ultrafiltration has been completed, it is set at pH 7 again with dilute sodium hydroxide solution, the retentate is frozen and freeze-dried. 6.78 g (97% of theory) of slightly yellowish, flocculent powder is obtained. Analytical sample-dyeing with ninhydrin shows that free amino groups are no longer present in the thiourea conjugate.

Water content (Karl Fischer): 8.3%
Gd determination (AAS): 13.2%
Elementary analysis (relative to anhydrous substance):

| Cld: | C 42.41 | H 4.96 | Gd 14.61 | N 9.11 | Na 2.14 | S 2.98 |
|---|---|---|---|---|---|---|
| Fnd: | C 42.25 | H 5.10 | Gd 14.26 | N 9.01 | Na 1.79 | S 2.66 | i) Polyrotaxane that Consists of Polyethylene Glycol and the hexa-Gd-complex of the α-cyclodextrin that is Described in Example 4h 1.40 g (0.2 mmol) of the hexa-Gd complex of the α-cyclodextrin that is described in Example 4h is dissolved in 10 ml of water and mixed with 10 mg (6.9 μmol) of polyethylene glycol (Sigma, $M_W$=1450) while being stirred. The solution is irradiated for 10 minutes in an ultrasonic bath and then stirred overnight at room temperature. For separation of low-molecular components, filtering is done using a 15 ml AMICON® centrifuging unit centriplus-3® and then freeze-dried. 560 mg of slightly yellowish, flocculent lyophilizate is obtained:

H₂O content (Karl Fischer): 9.3%

Gd determination (AAS): 12.9%

Elementary analysis (relative to anhydrous substance):

| | | | | | | |
|---|---|---|---|---|---|---|
| Cld: | C 42.57 | H 5.02 | Gd 14.42 | N 8.99 | Na 2.11 | S 2.94 |
| Fnd: | C 42.33 | H 5.00 | Gd 14.20 | N 9.09 | Na 1.98 | S 2.77 |

Photon correlation spectroscopy shows numerical mean value; of >30 nm for the hydrodynamic particle size.

EXAMPLE 5 a) Hexaamide Derivative of 2,4,6-triiodo-3-N-(2-hydroxyethyl)-5-(hydroxy)acetatamido-isophthalic Acid with 6,6',6'',6''',6'''',6'''''-hexaamino-6,6',6'',6''',6'''',6'''''-hexadeoxy-α-cyclodextrin 2.02 g (20 mmol) of triethylamine and 5.03 g (6.60 mmol) of the acid chloride of 2,4,6-triiodo-3-N-(2-acetoxyethyl)-5-acetoxy-acetamido-isophthalic acid [Guerbet S. A., WO 93/10824] are added to 1.26 g (1 mmol) of 6,6',6'',6''',6'''', 6'''''-hexaamino-6,6',6'',66''',6'''',6'''''-hexadeoxy-α-cyclodextrin-hexahydrochloride [J. Boger, R. J. Corcorcan and J.-M. Lehn, Helv. Chim. Acta 61, 2190–2218 (1978)] in 40 ml of N,N-dimethylacetamide. It is stirred for 24 hours at room temperature. It is evaporated to the dry state in a vacuum, the residue is dissolved in 200 ml of methylene chloride and washed twice with 100 ml of 5% aqueous hydrochloric acid and 100 ml of 5% sodium carbonate solution each. The organic phase is evaporated to the dry state in a vacuum, the residue is dissolved in 200 ml of methanol, and ammonia (gas) is introduced at 0° C. until saturation is reached. It is stirred for 6 hours at 0° C., then for 1 hour at 40° C. It is evaporated to the dry state, and the residue is chromatographed on an RP-18 column (mobile solvent: gradient that consists of water/acetonitrile/n-propanol).

Yield: 4.1 g (85% of theory) of a colorless solid

Water content: 1.2%

Elementary analysis (relative to anhydrous substance):

| | | | | |
|---|---|---|---|---|
| Cld: | C 26.92 | H 2.51 | N 5.23 | J 47.41 |
| Fnd: | C 26.71 | H 2.70 | N 5.05 | J 47.19 | b) Polyrotaxane that Consists of Methoxypolyethylene Glycol (M=2000) and the a-cyclodextrin-hexa-amide that is Described under Example 5a 936.7 mg (0.2 mmol) of the title compound from Example 5a is dissolved in 5 ml of water and mixed with 10 mg (5 μmol) of methoxypolyethylene glycol (Sigma, M=2000) while being stirred. The solution is irradiated for 10 minutes in an ultrasonic bath and then stirred overnight at room temperature. For separation of low-molecular components, it is filtered via a 15 ml AMICON® centrifuging unit centriplus-3® (cut off 3,000 Dalton) and then, freeze-dried. 389 mg of colorless, flocculent lyophilizate is obtained.

Water content: 3.9%

Elementary analysis (relative to anhydrous substance):

| | | | | |
|---|---|---|---|---|
| Cld: | C 29.23 | H 3.07 | N 4.79 | J 43.44 |
| Fnd: | C 29.01 | H 3.19 | N 4.61 | J 43.28 |

Photon correlation spectroscopy shows numerical mean values of >25 nm for the hydrodynamic particle size.

What is claimed is:

1. Pseudopolyrotaxanes that contain metal complex-containing or iodine-containing benzene derivatives as imaging components for MRT diagnosis and diagnostic radiology.

2. Pseudopolyrotaxane of formula I

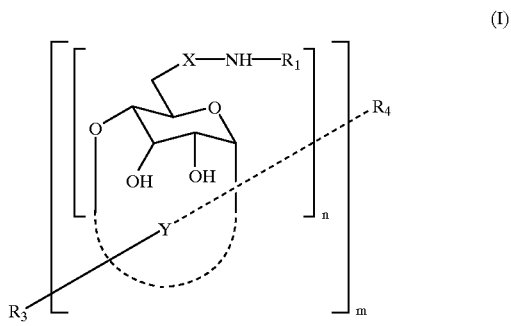

(I)

in which n means the numbers 6, 7 or 8, m means the numbers 2 to 50,

X means a direct bond or the radical —O—CO—CH(CH₃)—,

R₁ means the opacifying radicals

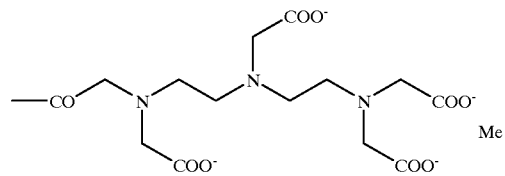

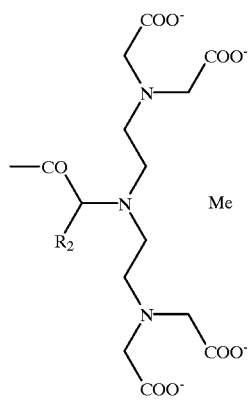

-continued

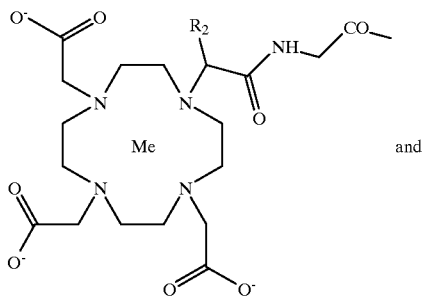

and

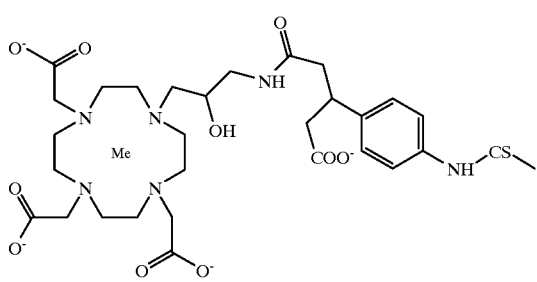

with R₂ meaning hydrogen, —(CH₂)₁₋₃—COOH, straight-chain or branched (C₁–C₄)-alkyl, straight-chain or branched (C₁–C₄)-hydroxyalkyl, phenyl or benzyl, Me as a metal cation of an element of atomic numbers 21 to 29, 39, 42, 44 or 57–83 as well as optionally cations of inorganic and/or organic bases, amino acids or amino acid amides or R₁ meaning

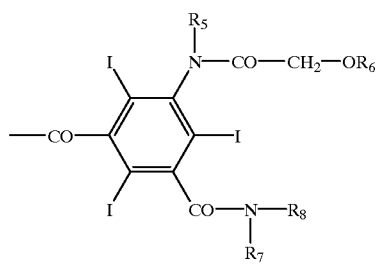

with

R₅ meaning hydrogen or C₁–C₂ alkyl or a —(CH₂)₁₋₃—COOH group,

R₆ meaning hydrogen or methyl, and

R₇, R₈, the same or different, meaning hydrogen or straight-chain alkyl with 2–6 C atoms or branched-chain alkyl with 3–6 C atoms, whereby both alkyl radicals can be substituted with 1–5 OH groups, R₃ stands for a hydroxy or C₁–C₂ alkoxy group, R₄ stands for a hydroxy, methyl or methoxy group, Y means radicals —(CH₂)ₚ[O—CH₂—CH₂]ₒ,

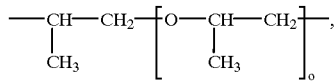

in which o means the numbers 10–200, and p means the numbers 2–20 or

Y means the radical —[CH₂]₁₀—CO—NH—[CH₂]₂—, whereby in the latter case, R₄ stands for —N(R₁₀)—Z[N(R₁₀)₂]₂ and R₃ stands for radical —NH R₉, in which R₉ represents hydrogen, benzyloxycarbonyl,

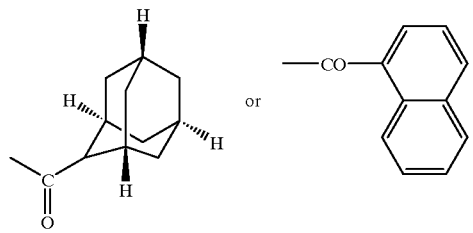

R₁₀ represents the radical

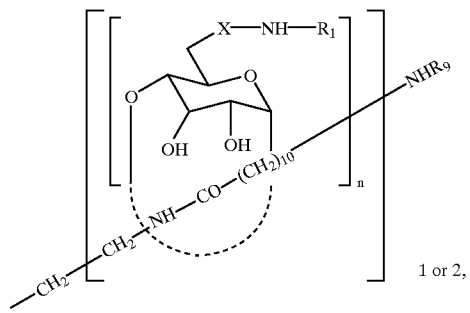

1 or 2, with the above-indicated meanings for n, R₁ and R₉, and

Z represents the radical

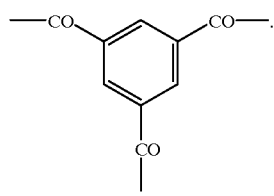

3. Pharmaceutical agents that contain at least one pseudopolyrotaxane complex according to claim 2, optionally with the additives that are commonly used in galenicals.

4. Use of at least one pseudopolyrotaxane complex according to claim 2 for the production of agents for NMR diagnosis or diagnostic radiology.

5. Use of at least one pseudopolyrotaxane complex according to claim 2 for the production of agents for angiography.

6. Use of at least one pseudopolyrotaxane complex according to claim 2 for the production of agents for lymphography.

7. Process for the production of pseudopolyrotaxane complexes according to claim 2, characterized in that compounds of formula II,

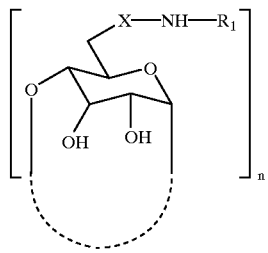
(II)

in which X, $R_1$ and n have the above-indicated meanings, are reacted with compounds of Formula III $$R_3—Y—R_{11} \quad (III),$$

in which Y and $R_3$ have the above-indicated meanings, and $R_{11}$ means hydroxy, methyl, methoxy or, if Y stands for —$(CH_2)_{10}$—CO—NH$(CH_2)_2$, the radical —N$(R_{12})$Z[N$(R_{12})_2]_2$, $R_{12}$ represents the radical —$(CH_2)_2$—NH—CO—$(CH_2)_{10}$—NHR$_9$ with $R_9$ in the above-indicated meaning.

8. A pseudopolyrotoxane of claim 1 having a complex of N,N,N',N',N'',N''-hexakis[14-benzyloxycarbonylamino)-4-oxo-3-aza-tetradecyl]trimesic acid triamide and hepta-(Gd-DTPA-monoamide) derivative of 6',6'',6''',6'''',6''''',6''''''-heptaamino-6',6'',6''',6'''',6''''',6''''''-heptadeoxy-β-cyclodextrin as the metal complex-containing benzene derivative.

* * * * *